United States Patent [19]

Felix et al.

[11] 4,442,031

[45] Apr. 10, 1984

[54] IMMUNOPOTENTIATING PEPTIDES

[75] Inventors: Arthur M. Felix, West Caldwell, N.J.; Hideo Ishitsuka, Yokohama, Japan; Johannes A. Meienhofer, Upper Montclair, N.J.; Yumiko Ohta, Zushi, Japan

[73] Assignee: Hoffmann-La Roche Inc., Nutley, N.J.

[21] Appl. No.: 482,347

[22] Filed: Apr. 5, 1983

Related U.S. Application Data

[63] Continuation of Ser. No. 311,569, Oct. 15, 1981, which is a continuation-in-part of Ser. No. 282,571, Jul. 13, 1981, abandoned.

[51] Int. Cl.$^3$ ............................................. C07C 103/52
[52] U.S. Cl. ............................................. 260/112.5 R
[58] Field of Search ................................. 260/112.5 R

[56] References Cited

U.S. PATENT DOCUMENTS 4,190,647 2/1980 Goldstein et al. ............ 260/112.5 R
4,361,673 11/1982 McGregor .................... 260/112.5 R Primary Examiner—Delbert R. Phillips
Attorney, Agent, or Firm—Jon S. Saxe; Bernard S. Leon; George M. Gould

[57] ABSTRACT

Novel hexapeptides corresponding to internal fragments of thymosin $\alpha_1$ are active as agents which restore and stimulate immune function.

3 Claims, No Drawings

IMMUNOPOTENTIATING PEPTIDES

CROSS-REFERENCE TO RELATED APPLICATION

This is a continuation of application Ser. No. 311,569 filed Oct. 15, 1981 which is a continuation-in-part of Ser. No. 282,571, filed July 13, 1981, now abandoned.

BACKGROUND OF THE INVENTION

Several polypeptide factors present in the thymus gland have been implicated to play an important role in the development and maintenance of immunological competence in man and in animals. The importance of the immune system in the defense against cancer and tumor cells is now widely recognized. In recent years, a few polypeptides shown to be able to stimulate maturation, differentiation and function of T cells have been isolated from bovine thymus. Among them, the peptide thymosin $\alpha_1$ has been intensively studied. Its structure and activity have been described in U.S. Pat. No. 4,079,127.

DESCRIPTION OF THE INVENTION

The present invention relates to novel hexapeptides represented by the formula

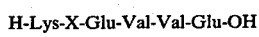

H-Lys-X-Glu-Val-Val-Glu-OH    I wherein X is -Lys- or -Ser-

The compound of formula I in which X is -Lys- corresponds to the amino acid residue sequence in positions 19-24 of thymosin $\alpha_1$.

The compounds of the present invention can be prepared by removal of protecting groups from corresponding protected peptides using procedures well known in the art for removal of such protecting groups. Thus, for example, the compounds of formula I of the present invention can be readily prepared from the corresponding protected peptides of the formula

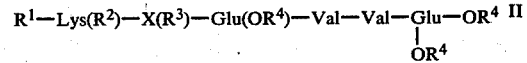

$R^1$—Lys($R^2$)—X($R^3$)—Glu(O$R^4$)—Val—Val—Glu—O$R^4$    II
                                                |
                                              O$R^4$ wherein $R^1$ is a conventional $\alpha$-amino protecting group, which may be selected from benzyloxycarbonyl which may be optionally substituted in the aromatic ring such as by 4-chloro, 2-bromo, 4-bromo, 2,4-dichloro, 4-nitro, 4-methoxy, 3,5-dimethoxy, 4-methyl, 2,4,6-trimethyl, 4-phenylazo, 4-(4'-methoxyphenylazo), 2-(N,N-dimethylcarbonamido), 4-dihydroxyboryl, and 2-nitro-4,5-dimethoxy; urethane type protecting groups such as 4-toluenesulfonylethyloxycarbonyl, 9-fluorenylmethyloxycarbonyl and related base cleavable groups, 5-benzisoxazolylmethylene-oxycarbonyl, methylthio- and methylsulfonylethyloxycarbonyl, isonicotinyloxycarbonyl, haloethyloxycarbonyl, diisopropylmethyloxycarbonyl, benzhydryloxycarbonyl, isobornyloxycarbonyl, dinitrodiphenylmethyloxycarbonyl, tert.-butyloxycarbonyl, tert.-amyloxycarbonyl, adamantyloxycarbonyl, cyclopentyloxycarbonyl, methylcyclohexyloxycarbonyl, 2-arylisopropyloxycarbonyl groups such as 2-(p-biphenylyl)isopropyloxycarbonyl, 2-(4-pyridyl)isopropyloxycarbonyl and related nitrogen containing urethane groups; acyl groups, such as formyl, trifluoroacetyl, phthaloyl, benzenesulfonyl, acetoacetyl, chloroacetyl, 2-nitrobenzoyl, 4-toluenesulfonyl; sulfenyl groups such as benzenesulfenyl, o-nitrophenylsulfenyl and related sulfenyl groups; and aryl-lower alkyl groups such as diphenylmethyl and triphenylmethyl; $R^1$ preferably being benzyloxycarbonyl (Z); $R^2$ is a conventional protecting group for the amino side chain, which may be selected from any of the protecting groups set forth in $R^1$, and is preferably t-butyloxycarbonyl (Boc); when X is -Ser-, $R^3$ is a conventional protecting group for the hydroxyl side chain, such as t-butyl or benzyl, preferably t-butyl; when X is -Lys-, $R^3$ is a conventional protecting group for the amino side chain, which may be selected from any of the protecting groups set forth in $R^1$, and is preferably t-butyloxycarbonyl (Boc); and $R^4$ in each instance is a conventional protecting group for carboxyl groups, for example, esters, such as aryl esters, particularly phenyl or phenyl substituted with lower alkyl, halo, nitro, aralkyl esters, such as benzyl or benzyl substituted with methoxy, halo, or nitro, lower alkyl esters, such as methyl, ethyl, t-butyl or t-amyl, substituted lower alkyl esters and phenacyl esters, by removal of the protecting groups in a manner known per se.

Preferred compounds of formula II are

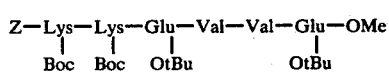

Z—Lys—Lys—Glu—Val—Val—Glu—OMe    IIa
    |    |    |              |
   Boc  Boc  OtBu           OtBu and

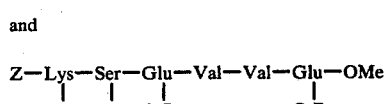

Z—Lys—Ser—Glu—Val—Val—Glu—OMe    IIb
    |    |    |              |
   Boc  tBu  OtBu           OtBu wherein tBu is t-butyl, OtBu is t-butyloxy and Me is methyl.

The protecting groups of the compounds of formulas IIa and IIb can be conveniently removed by catalytic hydrogenation, preferably in the presence of a palladium catalyst, saponification with NaOH and treatment with trifluoroacetic acid (TFA).

A protected hexapeptide of formula II in which X is -Lys- can be prepared by the reaction of

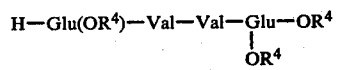

H—Glu(O$R^4$)—Val—Val—Glu—O$R^4$
                            |
                          O$R^4$ and $R^1$-Lys($R^2$)-Lys($R^3$)-OH using dicyclohexyl-carbodiimide (DCC) and N-hydroxysuccinimide (HOSu). A protected hexapeptide of formula II in which X is -Ser- can be prepared by the reaction of

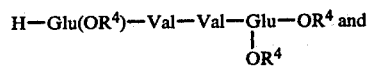

H—Glu(O$R^4$)—Val—Val—Glu—O$R^4$ and
                            |
                          O$R^4$

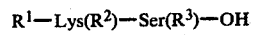

$R^1$—Lys($R^2$)—Ser($R^3$)—OH using DCC and hydroxybenzotriazole (HOBt).

The tetrapeptide

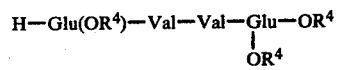

H—Glu(O$R^4$)—Val—Val—Glu—O$R^4$
                            |
                          O$R^4$ can be prepared by hydrogenation in the presence of a suitable hydrogenation catalyst (e.g. Pd on carbon, Pd on BaSO$_4$ or the like), of the compound

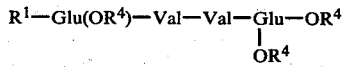

in which the R⁴ protecting groups are groups which are stable under the conditions which reduce the R¹ group.

The dipeptide R¹-Lys(R²)-Ser(R³)-OH can be prepared by the reaction of R¹-Lys(R²)-OSu and H-Ser(R³)-OH.

The preparation of compounds of this invention, employing preferred protecting groups, is illustrated in the reaction scheme below:

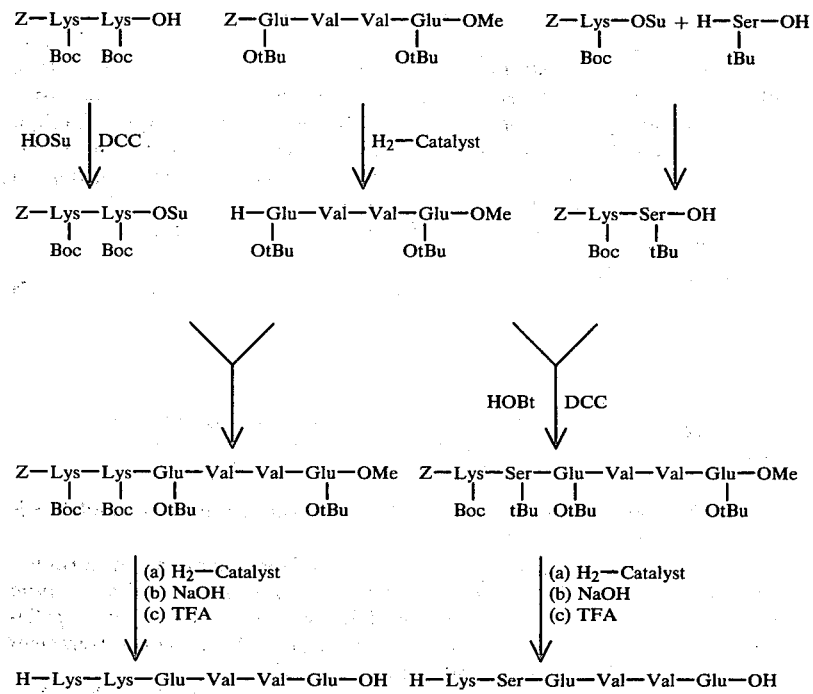

The protected tetrapeptide Z-Glu(OtBu)-Val-Val-Glu(OtBu)-OMe, which is a starting material in the foregoing reaction scheme, can be conveniently prepared by reacting HCl.H-Glu(OtBu)-OMe with Z-Val-OH by the mixed anhydride procedure (in the presence of isobutylchloroformate) at −15° C. to produce Z-Val-Glu(OtBu)-OMe; hydrogenating the resultant compound in the presence of a suitable hydrogenation catalyst to produce H-Val-Glu-(OtBu)-OMe; coupling the compound thus produced with Z-Val-OH by the mixed anhydride method (in the presence of isobutylchloroformate) to produce the tripeptide Z-Val-Val-Glu(OtBu)-OMe; hydrogenating the resulting tripeptide in the presence of a suitable hyrogenation catalyst; and coupling the resultant compound, i.e. H-Val-Val-Glu(OtBu)-OMe, with Z-Glu(OtBu)-OH by the mixed anhyride method (in the presence of isobutylchloroformate).

The compounds of formula I of the present invention have activity in the restoration and stimulation of immune function. Thus, they are useful, for example, in the treatment of opportunistic infections in an immunosuppressed host. Such activity must be considered unexpected in view of the knowledge in the peptide hormone art that the deletion of even one amino acid from the sequence of a biologically active peptide, e.g. thymosin $\alpha_1$, can result in the loss of biological activity. This is particularly true for relatively small peptide molecules.

The compounds of formula I and salts thereof may be used as medicaments; for example, in the form of pharmaceutical preparations which contain them in association with a compatible pharmaceutical carrier material. This carrier material can be an organic or inorganic carrier material suitable for enteral (e.g. oral) or parenteral administration (e.g. intravenous, subcutaneous or intramuscular). Examples of such carrier materials are water, lactose, starch, magnesium stearate, gum arabic, gelatin, polyalkyleneglycols, petroleum jelly and the like. The pharmaceutical preparations can be prepared in solid form (e.g. as tablets, dragees, suppositories or capsules) or in a liquid form (e.g. as solutions, suspensions, emulsions or ointments). The pharmaceutical preparations may be subjected to conventional pharmaceutical operations such as sterilization and may contain conventional adjuvants such as preservatives, stabilizers, wetting agent or salts for altering the osmotic pressure.

The pharmaceutical preparations can be prepared according to methods well known in the art.

They can be administered etiher orally or parenterally from once a day up to four times a day. The oral dosage form preferably contains 0.01–100 mg, the parenteral dosage form 1 μg–10 mg of active ingredient.

The acute toxicity of the compounds of formula I is low. Mice did not exhibit symptoms of toxicity when administered compounds of formula I, either orally or intraperitonially, at doses as high as 500 mg/kg.

The present invention is further illustrated by the examples which follow. In the examples, all amino acid derivatives were of the L-configuration. TLC was carried out on silica gel G plates and developed with chlorine-TDM. Melting points were determined on the Hoover apparatus (with correction) or on a Reichert hot stage apparatus (without correction). Optical rotations were measured in a jacketed 1-dm cell on a Perkin Elmer Model 141 Polarimeter. Amino acid analyses were performed on the Beckman Model 121M Amino Acid Analyzer. In the Examples, the following designations are used to identify the compounds of the invention:

Compound A: H-Lys-Lys-Glu-Val-Val-Glu-OH
Compound B: H-Lys-Ser-Glu-Val-Val-Glu-OH

EXAMPLE 1

γ-t-Butyl-L-glutamyl-L-valyl-L-valyl-γ-t-butyl-L-glutamic acid methyl ester

A solution of Z-Glu(OtBu)-Val-Val-Glu(OtBu)-OMe (1.57 g, 2.14 mmol) in dimethylformamide (DMF) (20 ml) was hydrogenated with 5% PD-BaSO$_4$(0.5 g) for 3 hours in a Vibromixer apparatus. The reaction mixture was filtered through celite and evaporated in vacuo to yield 1.21 g (94%); mp 177°–178°; $[\alpha]_D^{25}$ −17.49°(c 1, DMF); R$_f$ 0.74 (n-BuOH:EtOAc:H$_2$O:AcOH; 1-1-1-1); R$_f$ 0.29 (CHCl$_3$:CH$_3$OH:AcOH; 80-20-5). Anal. calc. for C$_{29}$H$_{52}$N$_4$O$_9$ (600.75): C, 57.98; H, 8.73; N, 9.33. Found: C, 57.56; H, 8.71; N, 9.39.

EXAMPLE 2

N$^\alpha$-Benzyloxycarbonyl-N$^\epsilon$-t-butyloxycarbonyl-L-lysly-N$^\epsilon$-t-butyloxycarbonyl-L-lysine hydroxysuccinimide ester A solution of Z-Lys(Boc)-Lys(Boc)-OH gnerated from Z-Lys(Boc)-Lys(Boc)-OH.DCHA (7.0 g, 0.0089 mol) in CH$_2$Cl$_2$:DMF (50 ml:3 ml) was cooled to 0°. N-hydroxysuccinimide (1.024 g, 0.0089 mol) and dicyclohexylcarbodiimide (1.833 g, 0.0089 mol) were added. Stirring continued at 0° for 1 hour and 25° for 16 hours. The reaction mixture was filtered and evaporated to dryness. The residue was crystallized from ethanol-ethyl acetate to give 2.67 g (42.5%) of white solid; mp 158°–160° dec; $[\alpha]_D^{25}$ −6.32° (c 1, DMF). Anal. calc. for C$_{34}$H$_{51}$N$_5$O$_{11}$H$_2$O (723.8): C, 56.42; H, 7.38; N, 9.68. Found: C, 56.57; H, 7.06; N, 9.92.

EXAMPLE 3

N$^\alpha$-Benzyloxycarbonyl-N$^\epsilon$-t-butyloxycarbonyl-L-lysyl-N$^\epsilon$-t-butyloxycarbonyl-L-lysyl-γ-t-butyl-L-glutamyl-L-valyl-L-valyl-γ-t-butyl-L-glutamic acid methyl ester A solution of Z-Lys(Boc)-Lys(Boc)-OSu (0.565g, 0.8 mmol) in DMF (6 ml) was immersed in an ice bath and H-Glu(OtBu)-Val-Val-Glu(OtBu)-OMe (0.481 g, 0.8 mmol) in DMF (6 ml) was added. The reaction mixture was stirred magnetically at 0° for 1 hour and 25° for 70 hours and the pH was maintained at about 8 by the periodic addition of triethylamine. The reaction mixture was evaporated to a white solid which was triturated with H$_2$O and filtered to yield 0.93 g (98%); m; 240°–241°; $[\alpha]_D^{25}$ −18.31° (c 1, DMF); R$_f$ 0.70 (CHCl$_3$:CH$_3$OH:AcOH; 80-5-1). Anal. calc. for C$_{59}$H$_{98}$N$_8$O$_{17}$ (1191.43): C, 58.48; H, 8.29; N, 9.40. Found: C, 58.65; H, 8.11; N, 9.31.

EXAMPLE 4

L-Lysyl-L-lysyl-L-glutamyl-L-valyl-L-valyl-L-glutamic acid

A solution of Z-Lys(Boc)-Lys(Boc)-Glu(OtBu)-Val-Glu(OtBu)-OMe (0.40 g, 0.34 mmol) in trifluoroethanol (TFE) (10 ml) was hydrogenated with 5% Pd-BaSO$_4$(0.15 g) for 4 hours in a Vibromixer apparatus. The reaction mixture was filtered through celite and evaporated to yield 0.305 g (0.29 mmol). This intermediate was taken up in CH$_3$OH (2.5 ml) and 1N NaOH (0.73 ml, 2.5 eq.) was added portionwise over a period of 5 hours. The reaction mixture was acidified with 2N HCl (0.36 ml) and cooled to 0°. The solid was collected and dried to yield 0.189 g which was reacted with TFA:CH$_2$Cl$_2$(1:1, 3 ml) by stirring at 25° under nitrogen for 3 hours. The solution was evaporated, then reevaporated from CH$_2$Cl$_2$(4 times). This crude product was taken up in 5 ml of 2% NH$_4$OAc (pH 8.1) and applied to a Dowex 1×2 column. It was eluted with 0.02 M AcOH followed by a gradient elution (0.02 M AcOH to 1.0 M AcOH). Fractions of 50 drops (2.65 ml) were collected and the product region visualized by developing aliquots of individual fractions on TLC. Fractions 9–13 (24–35 ml) were pooled and lyophilized to yield 0.115 g; m; 206°–215° dec.; $[\alpha]_D^{25}$ −75.27° (c 1, 0.1 M HCl); R$_f$ 0.31 (n-BuOH:Pyr:AcOH:H$_2$O; 15-10-3-12); R$_f$ 0.19 (n-BuOH:H$_2$O:AcOH:EtOAc; 1-1-1-1). Amino Acid Anal. (Leucine aminopeptidase; 37°, 24 h): Glu, 2.06; Val, 1.97; Lys, 1.97. Anal. calc. for C$_{32}$H$_{58}$N$_8$O$_{11}$2H$_2$O (766.88): C, C, 50.12; H, 8.15; N, 14,61; H$_2$O, 4.70. Found: C, 50.49; H, 8.11; N, 14.65; H$_2$O, 6.64.

EXAMPLE 5

N$^\alpha$-Benzyloxycarbonyl-N$^\epsilon$-t-butyloxycarbonyl-L-lysyl-O-t-butyl-L-serine A solution of H-Ser(tBu)-OH (0.337 g, 2.09 mmol), pre-ground in a mortar, and Z-Lys(Boc)-OSu (1.0 g, 2.09 mmol) was stirred magnetically in dry DMF (11 ml). It was chilled in an ice-bath for 5 minutes and triethylamine (0.29 ml, 2.09 mmol) was added. The temperature was maintained at 0° for 20 minutes, the ice-bath was removed, and an additional 0.2 ml of triethylamine was added to pH 7.5–8.0. The solution was stirred at 25° for 24 hours, and evaporated in vacuo to an oil. The oil was dissolved in ethyl acetate (15 ml) and washed with 1 M citric acid (3×8 ml) and water (3×10 ml). The ethyl acetate was dried (Na$_2$SO$_4$), filtered and evaporated to yield a colorless oil (1.12 g). The oil was dissolved in anhydrous ether (27 ml) and dicyclohexylamine (0.42 ml, 2.09 mmol) was added. Addition of petroleum ether to the cloud point resulted in crystallization. The precipitate was collected by filtration, washed well with anhydrous ether and dried to afford 0.939 g (63.9%) of white crystalline solid; mp 147°–149°. Recrystallization from CH$_2$Cl$_2$-ether-petroleum ether gave an analytical sample: mp 150°–151.5°; R$_f$ 0.41 (DCHA) and 0.68 (free acid) (CHCl$_3$:MeOH:AcOH; 85-10-5); $[\alpha]_D^{25}$ +10.78° (c 1, MeOH). Anal. Calc. for C$_{38}$H$_{64}$N$_4$O$_8$ (704.95): C, 64.74; H, 9.15; N, 7.95. Found: C, 64.76; H, 8.99; N, 8.06.

The free acid was generated as follows: The above DCHA salt (0.63 g, 0.894 mmol) was extracted with EtOAc:0.1N H$_2$SO$_4$ and the organic layer was retained, washed with water, 70% brine, dried (Na$_2$SO$_4$) and evaporated to dryness to yield 446 mg (9.53%) of white solid; R$_f$ 0.68 (CHCl$_3$:MeOH:AcOH; 85-10-5); $[\alpha]_D^{25}$ +17.58 (c 1, CHCl$_3$). Anal. calc. for C$_{26}$H$_{41}$N$_3$O$_8$ (523.63): C, 59.64; H, 7.89; N, 8.02. Found: C, 59.36; H, 7.82; N, 7.88.

EXAMPLE 6

N$^\alpha$-Benzyloxycarbonyl-N$^\epsilon$-t-butyloxycarbonyl-L-lysyl-O-t-butyl-L-seryl-γ-t-butyl-L-glutamyl-L-valyl-L-valyl-γ-t-butyl-L-glutamic acid methyl ester A solution of Z-Lys(Boc)-Ser(tBu)-OH (392 mg, 0.749 mmol) and H-Glu(OtBu)-Val-Val-Glu(OtBu)-

OMe, (391 mg, 0.651 mmol) in DMF (9 ml) was immersed in an ice bath and hydroxybenzotriazole (249 mg, 1.63 mmol) and DCC (168 mg, 0.814 mmol) were added. The reaction mixture was stirred magnetically at 0° for 1 hour and 25° for 16 hours. N-Methylmorpholine (0.18 ml, 1.63 mmol) was added periodically to maintain pH 7.5-8. The reaction mixture was precipitated by addition of 230 ml 5% AcOH. It was filtered, washed with $H_2O$, MeOH, ether and petroleum ether and dried in vacuo to give 516 mg of product. Reprecipitation from DMF-$H_2O$ afforded 470 mg (65.3%) final product; mp 256°-257°; $R_f$ 0.4 (CHCl$_3$:MeOH:AcOH; 80-5-1): $[\alpha]_D^{25}$ −46.81° (c 1, Trifluoroethanol). Anal. calc. for $C_{55}H_{91}N_7O_{16}$ (1106.37): C, 59.71; H, 8.29; N, 8.86. Found: C, 59.49; H, 8.22; N, 9.11.

EXAMPLE 7

L-Lysyl-L-seryl-L-glutamyl-L-valyl-L-valyl-L-glutamic acid

A solution of Z-Lys(Boc)-Ser(tBu)-Glu(OtBu)-Val-Val-Glu(OtBu)-OMe (0.40 g, 0.362 mmol) in TFE (8 ml) was hydrogenated with 10% Pd-C (0.15 g) for 2.5 hours in a Vibromixer apparatus. The reaction mixture was filtered through celite and evaporated to yield 370 mg; $R_f$ 0.19 CHCl$_3$:MeOH:AcOH; 85-10-5). This intermediate was taken up in THF (9 ml):$H_2O$ (2.5 ml) and 1N NaOH (0.47 ml, 1.30 eq.) added. Stirring continued for 2.5 hours and the reaction mixture was acidified with 1N HCl (0.47 ml). The precipitate was filtered, washed with $H_2O$, ether and dried in vacuo to yield 253 mg of white solid. This crude intermediate was reacted with TFA:CH$_2$Cl$_2$ (1:1, 4 ml) by stirring at 25° for 3.5 hours. The solution was evaporated, then reevaporated from CH$_2$Cl$_2$ (4 times). This crude product was taken up in 2 ml of 2% NH$_4$OAc (pH 8.1) and applied to a Dowex 1×2 column (20×1.5 cm). It was eluted with 0.02 M AcOH followed by a gradient elution (0.02 M AcOH to 1.0 M AcOH). Fractions of 40 drops (2.12 ml) were collected and the product region visualized by developing aliquots of individual fractions on TLC. Fractions 13-26 (27-55 ml) were pooled and lyophilized to yield 143 mg (51.4% for the three reactions); mp 220°-225° dec; $[\alpha]_D^{25}$ −74.33° (c 0.26, 0.1 M HCl); $R_f$ 0.23 (n-BuOH:AcOH:EtOAc:$H_2O$; 1-1-1-1). Amino Acid Anal. (Leucine aminopeptidase; 37°, 24 h): Glu, 2.01; Val, 1.97; Lys, 1.03; Ser, 0.99. Anal. calc. for $C_{29}H_{51}N_7O_{12}$.4$H_2O$ (761.83); C, 45.72; H, 7.81; N, 12.87. Found: C, 45.15; H, 7.20; N, 12.66.

EXAMPLES 8-11

In a series of examples, the compounds of formula I were tested for protective activity against opportunistic infections in immunosuppressed mice. Female ddY mice (6 weeks old) weighing about 26 g were pretreated daily for ten days with 5-fluorouracil (5-FU) (25 mg/kg/day, i.p.) and with thymosin $\alpha_1$ or with compounds of formula I (i.p.) at varying dosages. The mice were then infected with *Candida albicans* ATCC 10231 (1×10$^5$ cells or more) at 24 hour after the last treatment. One control group was administered 5-FU and saline solution and a second control group received neither 5-FU nor compound of formula I prior to infection with *Candida albicans*. The number of animals surviving eight days after infection with *Candida albicans* and 15 days after infection with *Candida albicans* is presented in the table below.

As can be seen from Table 1, treatment with 5-FU made the mice susceptible to the infection with *Candida albicans*, while the control group which did not receive 5-FU pretreatment was highly resistant to infection. The protective effects against infection which were conferred by the compounds of formula I were comparable to the protective effects conferred by thymosin $\alpha_1$.

| Compound | Dose (μg/kg) | Survivors Day 8 | Day 15 |
|---|---|---|---|
| Example 8 | | | |
| Compound A* | 0.4 | 6/7 | 5/7 |
| | 4.0 | 5/7 | 4/7 |
| | 40.0 | 5/7 | 2/7 |
| Compound B** | 4.0 | 6/7 | 3/7 |
| | 40.0 | 3/7 | 3/7 |
| Thymosin $\alpha_1$ | 40.0 | 5/7 | 5/7 |
| Control (saline) | | 3/7 | 1/7 |
| Control (no 5-Fu) | | 7/7 | 7/7 |
| Example 9 | | | |
| Compound A | 0.4 | 6/7 | Not |
| | 4.0 | 5/7 | observed |
| | 40.0 | 4/7 | |
| Compound B | 4.0 | 5/7 | |
| | 40.0 | 5/7 | |
| Thymosin $\alpha_1$ | 40.0 | 4/7 | |
| Control (saline) | | 1/7 | |
| Control (no 5-FU) | | 7/7 | |
| Example 10 | | | |
| Compound A | 0.04 | 6/10 | 4/10 |
| | 0.4 | 9/10 | 8/10 |
| | 4.0 | 9/10 | 8/10 |
| Thymosin $\alpha_1$ | 0.4 | 3/10 | 3/10 |
| | 4.0 | 6/10 | 5/10 |
| | 40.0 | 9/10 | 8/10 |
| Control (saline) | | 4/10 | 3/10 |
| Control (no 5-FU) | | 10/10 | 10/10 |
| Example 11 | | | |
| Compound A | 0.04 | 6/10 | 4/10 |
| | 0.4 | 9/10 | 8/10 |
| | 4.0 | 9/10 | 8/10 |
| Thymosin $\alpha_1$ | 4.0 | 3/10 | 3/10 |
| | 40.0 | 6/10 | 5/10 |
| | 400.0 | 8/10 | 8/10 |
| Control (saline) | | 4/10 | 3/10 |
| Control (no 5-FU) | | 10/10 | 10/10 |

*Compound A = H—Lys—Lys—Glu—Val—Val—Glu—OH
**Compound B = H—Lys—Ser—Glu—Val—Val—Glu—OH

EXAMPLE 12

Restoration of impaired cell-mediated immunity

A poor prognosis is often observed in cancer patients with impaired immune response. Impaired immune response can be caused by the cancer itself, by chemotherapeutic agents, or by radiotherapy. Thus, therapeutic agents which restore impaired immune response in cancer patients are expected to play an important role in combination therapy. The restoration activity of the compounds of the invention on impaired cell-mediated immunity was determined by measuring the enhancement of delayed-type hypersensitivity (DTH), which was decreased to a great extent in mice treated with 5-fluorouracil (5-FU).

Female BDF$_1$ mice (20-22 g, 11-12 weeks old) received (i.p. or p.o.) the compound to be tested on consecutive days one day before, concurrently with and 1 and 2 days after the 5-FU treatment. For DTH measurement, 10$^8$ chicken red blood cells (CRBC) were injected i.p. (or s.c. into the left hind footpad) and challenged s.c. into the right hind footpad at 3 and 7 days after the 5-FU treatment, respectively. Restoration activity was calculated by the following formula from the DTH response observed in the control group, 5-FU treated group treatment and the Test group treated both with 5-FU and the compound of the invention. Restoration activity was calculated by the formula:

$$\text{Restoration activity} = \frac{\text{Test} - 5\text{-}FU}{\text{Control} - 5\text{-}FU} \times 100$$

As shown in Table 2, the Compound A exhibited equal or in some instances, greater activity than did thymosin $\alpha_1$ at lower doses. Compound B was also active (see Table 3). Further, Compound A was found to be active when administered orally (see Table 4).

mus gland, which is essential for differentiation, maturation and supply to T-cells responsible for immunological reactions, decreases markedly in weight after injection of 5-FU. Compound A, at a dosage of 50 μg/kg, was found to restore the decreased thymus weight when administered orally one day before, concurrently with, and 1 and 2 days after 5-FU injection (100 mg/kg) in the mice used for the DTH assay. FIfty μg/kg of Compound A administered orally was as effective as 5 μg/kg of thymosin $\alpha_1$ injected intraperitoneally, when the thymus weight was measured immediately after the DTH measurement at 8 days after the 5-FU injection (see Table 5).

TABLE 2

| Mice treated with | Dose μg/kg/day, i.p. | DTH response* av. ± S.E. (0.1 mm) | % | Restoration Activity(%) |
|---|---|---|---|---|
| control | — | 10.3 ± 1.0 | 100 | — |
| 5-FU alone | — | 5.7 ± 0.4 | 55.4 | — |
| 5-Fu plus thymosin $\alpha_1$ | 0.5 | 5.8 ± 1.1 | 56.0 | 1.3 |
|  | 5.0 | 8.0 ± 1.2 | 77.8 | 50.3 |
| 5-Fu plus Compound A | 0.05 | 7.3 ± 0.9 | 70.7 | 34.4 |
|  | 0.5 | 8.7 ± 1.2** | 84.8 | 66.6 |
|  | 5.0 | 8.3 ± 0.8** | 80.7 | 56.6 |

*7 mice per group
**$p < 0.05$

TABLE 3

| Mice treated with | Dose μg/kg/day, i.p. | DTH response* av. ± S.E.(0.1 mm) | % | Restoration Activity(%) |
|---|---|---|---|---|
| control | — | 8.5 ± 0.7 | 100 | — |
| 5-FU alone | — | 4.8 ± 0.6 | 56.2 | — |
| 5-FU plus thymosin $\alpha_1$ | 5.0 | 7.3 ± 0.8** | 86.3 | 68.7 |
| 5-FU plus Compound B | 0.05 | 7.2 ± 0.8** | 84.7 | 65.0 |
|  | 0.5 | 6.5 ± 0.7 | 77.2 | 48.0 |
|  | 5.0 | 8.5 ± 1.0*** | 100 | 100 |
| control | — | 15.1 ± 1.0 | 100 | — |
| 5-FU alone | — | 8.1 ± 0.6 | 53.1 | — |
| 5-FU plus Compound A | 0.5 | 10.8 ± 0.8** | 71.6 | 39.1 |
| 5-FU plus Compound B | 0.5 | 8.5 ± 0.9 | 56.4 | 6.5 |
|  | 5.0 | 8.3 ± 1.8 | 54.8 | 3.1 |
|  | 50.0 | 9.4 ± 0.8 | 61.9 | 18.3 |

*7 mice per group
**$p < 0.05$
***$p < 0.01$

TABLE 4

| Mice treated with | Dose μg/kg/day | Route | DTH response* av. ± S.E. (0.1 mm) | % | Restoration Activity(%) |
|---|---|---|---|---|---|
| control | — | — | 7.7 ± 1.1 | 100 | — |
| 5-FU alone | — | — | 5.6 ± 1.1 | 72.7 | — |
| 5-FU plus thymosin $\alpha_1$ | 0.5 | i.p. | 5.4 ± 1.2 | 70.1 | — |
|  | 5.0 | i.p. | 7.3 ± 0.8 | 94.8 | 81.0 |
| 5-FU plus Compound A | 0.5 | p.o. | 5.4 ± 0.9 | 70.1 | 0 |
|  | 5.0 | p.o. | 5.9 ± 1.0 | 76.6 | 14.3 |
|  | 50.0 | p.o. | 8.7 ± 1.2* | 113 | 147.6 |

*7 mice per group
*$p.<0.1$

EXAMPLE 13

Restoration of thymus weight decreased by 5-FU injection

It is known that anticancer drugs suppress immunological functions by affecting immunocytes. The thy-

TABLE 5

| Mice treated with | Dose μg/kg/day | Route | Av. thymus weight* mg | % | Restoration Activity(%) |
|---|---|---|---|---|---|
| control | — | — | 39.4 ± 1.7 | 100 | — |

TABLE 5-continued

| Mice treated with | Dose µg/kg/day | Route | Av. thymus weight* mg | % | Restoration Activity(%) |
|---|---|---|---|---|---|
| 5-FU alone | — | — | 23.4 ± 1.7 | 59.4 | — |
| 5-FU plus thymosin $\alpha_1$ | 0.5 | i.p. | 24.9 ± 1.7 | 63.2 | 9.4 |
|  | 5.0 | i.p. | 26.7 ± 1.1 | 67.8 | 20.6 |
| 5-FU plus Compound A | 5.0 | p.o. | 23.0 ± 1.6 | 58.4 | — |
|  | 50.0 | p.o. | 26.6 ± 1.0 | 67.5 | 20.0 |

*Seven mice per group received the test compound one day before, concurrently with, and 1 and 2 days after 5-FU injection i.p. (100 mg/kg). The mice were injected CRBC for The DTH assay at 3 and 7 days after the 5-FU injection.
The thymus weight was measured at 8 days after the 5-FU injection.

EXAMPLE 14

Protective activity against opportunistic infection (i) Microbial infections in immunosuppressed mice Normal mice (female ddY mice, 6 weeks old) were highly tolerant to infection with Candida albicans ATCC 10231 at relatively low dose (1–2×10⁵ cells, iv.). However, when pretreated daily for ten times with 5-FU (25 mg/kg/day, ip.), the mice were susceptible to infection as shown in Table 6. In this model for opportunistic infection, pretreatment daily for ten times with the compounds of the invention conferred protection against infection to an extent comparable to thymosin $\alpha_1$. Compound A was also shown to be active against infection with Pseudomonas aeruginosa 5E81-1 and Listeria monocytogenes EGD in the immunosuppressed mice (see Tables 7 and 8).

(ii) Microbial infection in tumor-bearing mice

The immunocompetence of tumor-bearing mice is known to be frequently deficient. This is illustrated by the fact that Listeria monocytogenes EGD grew considerably in tumor-bearing mice as compared to normal mice (see Table 9). Male $CDF_1$ mice (6 weeks old) transplanted with P388 leukemia (3×10⁵ cells, footpad) were infected with Listeria monocytogenes (2×10³ cells, iv.) 7 days after the transplant. Three days thereafter the number of the bacteria grown in liver was counted. In mice which were similarly infected, but which were also pretreated daily for seven times with the Compound A before infection, the growth of the bacteria was suppressed.

EXAMPLE 15

Protective activity against tumor growth in immunosuppressed mice

The treatment with cytostatic agents often decreases immunocompetence and consequently increases incidence of metastasis of tumor in cancer patients. The impairment of immune system against tumor growth was also demonstrated in mice treated with a cytostatic agent, 5FU. In the experiment shown in Table 10, male $CDF_1$ mice (6 week old) were treated daily for 8 times with or without 5-FU (28 mg/kg/day ip.) and then transplanted subcutaneously with P388 leukemic cells (3×10⁵) into footpad 24 hours later. When pretreated with 5-FU, mice died very quickly at 4 days, while normal mice survived about 23 days after the transplant. On the other hand, daily treatment with thymosin $\alpha_1$ or compound A in addititon to 5-FU for 8 times before and 6 times after the transplant increased the survival days to the level similar to that obtained in normal mice. Thymosin $\alpha_1$ and compound A may improve the immunodefense system against metastatic tumor growth in cancer patients who are receiving immunosuppressive chemotherapy. In combination with thymosin $\alpha_1$ or compound A, more extensive cancer chemotherapy for a longer duration may be possible.

TABLE 6

Infection with Candida albicans

| Compounds | Dose µg/kg/day, i.p. | Survivors* | $X^2$ test |
|---|---|---|---|
| Thymosin $\alpha_1$ | 40 | 4/7 | 0.01 |
| Compound A | 0.4 | 6/7 | 0.01 |
|  | 4 | 5/7 | 0.01 |
|  | 40 | 4/7 | 0.01 |
| Compound B | 4 | 5/7 | 0.01 |
|  | 40 | 5/7 | 0.01 |
| Control |  | 1/7 |  |
| Control (No 5-FU) |  | 7/7 | 0.01 |

*Survivors at Day 8 after infection.

TABLE 7

Infection Pseudomonas aeruginosa

| Compounds | Dose µg/kg/day, i.p. | Survivors* | $X^2$ test |
|---|---|---|---|
| Thymosin $\mu_1$ | 0.4 | 7/20 | 0.01 |
|  | 4 | 12/30 | 0.01 |
|  | 40 | 16/30 | 0.01 |
| Compound A | 0.04 | 5/20 | 0.01 |
|  | 0.4 | 12/30 | 0.01 |
|  | 4 | 7/30 | 0.01 |
| Control |  | 0/30 |  |
| Control (No 5-FU) |  | 30/30 | 0.01 |

*Survivors at Day 15 after infection.

TABLE 8

Infection with Listeria monocytogenes

| Compounds | Dose µg/kg/day, i.p. | Survivors* | $X^2$ test |
|---|---|---|---|
| Thymosin $\alpha_1$ | 4 | 7/10 | 0.01 |
|  | 40 | 5/10 | 0.01 |
| Compound A | 0.04 | 8/10 | 0.01 |
|  | 0.4 | 6/10 | 0.01 |
|  | 4 | 6/10 | 0.01 |
| Control |  | 2/10 |  |
| Control (No 5-FU) |  | 10/10 | 0.01 |

*Survivors at Day 15 after infection.

TABLE 9

| Compounds | Dose µg/kg/day, i.p. | Growth of Bacteria ($\log_{10}$/liver) |
|---|---|---|
| Tumor-bearing mice |  |  |
| Control |  | 7.1 |
| Thymosin $\alpha_1$ | 4 | 5.0 |
|  | 40 | 5.3 |
| Compound A | 0.4 | 6.0 |
|  | 4 | 5.7 |
| Normal mice |  |  |
| Control |  | 5.3 |

TABLE 10

| Treatment with 5-FU[1] | compound[2] | P388 Leukemia inoculation[3] | Mean Survival days[4] (days ± S.D.) | No. of mice tested |
|---|---|---|---|---|
| — | Saline | + | 23.3 ± 3.1 | 10 |
| + | Saline | — | 15.2 ± 12.8[5] | 9 |
| + | Saline | + | 4.1 ± 5.1 | 10 |
| + | Thymosin $\alpha_1$ 4 μg/kg/day | + | 17.6 ± 8.2 | 10 |
| + | 40 | + | 20.7 ± 2.8 | 10 |
| + | Compound A 0.4 μg/kg/day | + | 22.3 ± 2.8 | 10 |
| + | 4 | + | 23.7 ± 2.9 | 10 |

[1]CDF$_1$ mice were pretreated daily for 8 times from Day -8 to -1 with 5-FU (28 mg/kg/day, ip.).
[2]Thymosin $\alpha_1$ or Compound A were administered daily for 14 times from Day -8 to 5 by ip. route.
[3]P388 leukemic cells (3 × 10$^5$) were inoculated into footpad at Day 0.
[4]Survival days after the inoculation of the leukemic cells.
[5]Mean survival day for five mice died with toxicity was recorded and other four mice survived more than 40 days.

We claim:
1. A compound of the formula

H-Lys-X-Glu-Val-Val-Glu-OH wherein X is -Lys- or -Ser-, or a pharmaceutically acceptable salt thereof.

2. A compound of claim 1 which is H-Lys-Lys-Glu-Val-Val-Glu-OH.

3. A compound of claim 1 which is H-Lys-Ser-Glu-Val-Val-Glu-OH.

* * * * *